(12) United States Patent
Hanina et al.

(10) Patent No.: US 11,170,484 B2
(45) Date of Patent: *Nov. 9, 2021

(54) RECOGNITION OF SUSPICIOUS ACTIVITIES IN MEDICATION ADMINISTRATION

(71) Applicant: AIC Innovations Group, Inc., New York, NY (US)

(72) Inventors: Adam Hanina, New York, NY (US); Daniel Glasner, New York, NY (US); Li Zhang, Princeton, NJ (US); Chloe Chah, Long Island City, NY (US)

(73) Assignee: AIC Innovations Group, Inc., New York, NY (US)

( * ) Notice: Subject to any disclaimer, the term of this patent is extended or adjusted under 35 U.S.C. 154(b) by 114 days.

This patent is subject to a terminal disclaimer.

(21) Appl. No.: 16/135,858

(22) Filed: Sep. 19, 2018

(65) Prior Publication Data

US 2019/0087951 A1     Mar. 21, 2019

Related U.S. Application Data

(60) Provisional application No. 62/560,528, filed on Sep. 19, 2017.

(51) Int. Cl.
*G06T 7/00*     (2017.01)
*G16H 20/10*   (2018.01)
(Continued)

(52) U.S. Cl.
CPC ............ *G06T 7/0002* (2013.01); *G06F 21/32* (2013.01); *G06K 9/00536* (2013.01);
(Continued)

(58) Field of Classification Search
None
See application file for complete search history.

(56) References Cited

U.S. PATENT DOCUMENTS

| 3,814,845 A | 6/1974 | Hurlbrink et al. |
| 5,065,447 A | 11/1991 | Barnsley et al. |

(Continued)

FOREIGN PATENT DOCUMENTS

| CN | 102612703 A | 7/2012 |
| WO | WO 2004/103232 | 12/2004 |

(Continued)

OTHER PUBLICATIONS

International Search Report and Written Opinion for Int. App No. PCT/US2018/051669, dated Nov. 21, 2018 (8 pages).

(Continued)

*Primary Examiner* — Mohammad H Ghayour
*Assistant Examiner* — Pawan Dhingra
(74) *Attorney, Agent, or Firm* — Fish & Richardson P.C.

(57) ABSTRACT

Methods and systems for recognizing suspicious activities of a user administering a medication are described. One of the methods include capturing one or more video sequences of a user administering a medication by a video capture device; analyzing the captured one or more video sequences to determine one or more indications of a suspicious activity of the user; and adaptively performing a follow-up operation in response to a determination of one or more indications of a suspicious activity of the user.

26 Claims, 7 Drawing Sheets

(51) Int. Cl.
*H04N 7/18* (2006.01)
*G06K 9/00* (2006.01)
*G06F 21/32* (2013.01)
*G06T 7/20* (2017.01)
*G16H 50/30* (2018.01)
*G16H 10/60* (2018.01)
*G16H 50/20* (2018.01)
*G16H 40/67* (2018.01)
*G16H 10/20* (2018.01)

(52) U.S. Cl.
CPC ............ *G06K 9/00771* (2013.01); *G06T 7/20* (2013.01); *G16H 10/20* (2018.01); *G16H 10/60* (2018.01); *G16H 20/10* (2018.01); *G16H 40/67* (2018.01); *G16H 50/20* (2018.01); *G16H 50/30* (2018.01); *H04N 7/183* (2013.01); *H04N 7/188* (2013.01)

(56) References Cited

U.S. PATENT DOCUMENTS

| | | |
|---|---|---|
| 5,441,047 A | 8/1995 | David et al. |
| 5,544,649 A | 8/1996 | David et al. |
| 5,619,991 A | 4/1997 | Sloane |
| 5,646,912 A | 7/1997 | Cousin |
| 5,752,621 A | 5/1998 | Passamante |
| 5,764,296 A | 6/1998 | Shin |
| 5,810,747 A | 9/1998 | Brudny et al. |
| 5,911,132 A | 6/1999 | Sloane |
| 5,961,446 A | 10/1999 | Beller et al. |
| 6,151,521 A | 11/2000 | Guo et al. |
| 6,233,428 B1 | 5/2001 | Fryer |
| 6,283,761 B1 | 9/2001 | Joao |
| 6,380,858 B1 | 4/2002 | Yarin et al. |
| 6,409,661 B1 | 6/2002 | Murphy |
| 6,421,650 B1 | 7/2002 | Goetz et al. |
| 6,483,993 B1 | 11/2002 | Misumi et al. |
| 6,484,144 B2 | 11/2002 | Martin et al. |
| 6,535,637 B1 | 3/2003 | Wootton et al. |
| 6,611,206 B2 | 8/2003 | Milanski et al. |
| 6,705,991 B2 | 3/2004 | Bardy |
| 6,879,970 B2 | 11/2005 | Shiffman et al. |
| 6,988,075 B1 | 1/2006 | Hacker |
| 7,184,047 B1 | 2/2007 | Crampton |
| 7,184,075 B2 | 2/2007 | Reiffel |
| 7,256,708 B2 | 8/2007 | Rosenfeld et al. |
| 7,277,752 B2 | 10/2007 | Matos |
| 7,304,228 B2 | 12/2007 | Bryden et al. |
| 7,307,543 B2 | 12/2007 | Rosenfeld et al. |
| 7,317,967 B2 | 1/2008 | DiGianfilippo et al. |
| 7,340,077 B2 | 3/2008 | Gokturk |
| 7,369,919 B2 | 5/2008 | Vonk et al. |
| 7,395,214 B2 | 7/2008 | Shillingburg |
| 7,415,447 B2 | 11/2008 | Shiffman et al. |
| 7,447,333 B1 | 11/2008 | Masticola et al. |
| 7,448,544 B1 | 11/2008 | Louie et al. |
| 7,562,121 B2 | 7/2009 | Berisford et al. |
| 7,627,142 B2 | 12/2009 | Kurzweil et al. |
| 7,657,443 B2 | 2/2010 | Crass et al. |
| 7,692,625 B2 | 4/2010 | Morrison et al. |
| 7,740,013 B2 | 6/2010 | Ishizaki et al. |
| 7,747,454 B2 | 6/2010 | Bartfeld et al. |
| 7,761,311 B2 | 7/2010 | Clements et al. |
| 7,769,465 B2 | 8/2010 | Matos |
| 7,774,075 B2 | 8/2010 | Lin et al. |
| 7,874,984 B2 | 1/2011 | Elsayed et al. |
| 7,881,537 B2 | 2/2011 | Ma et al. |
| 7,908,155 B2 | 3/2011 | Fuerst et al. |
| 7,912,733 B2 | 3/2011 | Clements et al. |
| 7,956,727 B2 | 6/2011 | Loncar |
| 7,983,933 B2 | 7/2011 | Karkanias et al. |
| 8,321,284 B2 | 11/2012 | Clements et al. |
| 9,679,113 B2 * | 6/2017 | Hanina ................ G16H 40/67 |
| 2001/0049673 A1 | 12/2001 | Dulong et al. |
| 2001/0056358 A1 | 12/2001 | Dulong et al. |
| 2002/0026330 A1 | 2/2002 | Klein |
| 2002/0027507 A1 | 3/2002 | Yarin et al. |
| 2002/0093429 A1 | 7/2002 | Matsushita et al. |
| 2002/0143563 A1 | 10/2002 | Hufford et al. |
| 2003/0164172 A1 | 9/2003 | Chumas et al. |
| 2003/0190076 A1 | 10/2003 | Delean |
| 2003/0225325 A1 | 12/2003 | Kagermeier et al. |
| 2004/0100572 A1 | 5/2004 | Kim |
| 2004/0107116 A1 | 6/2004 | Brown |
| 2004/0155780 A1 | 8/2004 | Rapchak |
| 2004/0168951 A1 | 9/2004 | Mackie |
| 2005/0144150 A1 | 6/2005 | Ramamurthy et al. |
| 2005/0149361 A1 | 7/2005 | Saus et al. |
| 2005/0180610 A1 | 8/2005 | Kato et al. |
| 2005/0182664 A1 | 8/2005 | Abraham-Fuchs et al. |
| 2005/0234381 A1 | 10/2005 | Niemetz et al. |
| 2005/0267356 A1 | 12/2005 | Ramasubramanian et al. |
| 2006/0066584 A1 | 3/2006 | Barkan |
| 2006/0218011 A1 | 9/2006 | Walker et al. |
| 2006/0238549 A1 | 10/2006 | Marks |
| 2007/0008112 A1 | 1/2007 | Covannon et al. |
| 2007/0008113 A1 | 1/2007 | Spoonhower et al. |
| 2007/0016443 A1 | 1/2007 | Wachman et al. |
| 2007/0030363 A1 | 2/2007 | Cheatle et al. |
| 2007/0118054 A1 | 5/2007 | Pinhas et al. |
| 2007/0118389 A1 | 5/2007 | Shipon |
| 2007/0194034 A1 | 8/2007 | Vasiadis |
| 2007/0233035 A1 | 10/2007 | Wehba et al. |
| 2007/0233049 A1 | 10/2007 | Wehba et al. |
| 2007/0233050 A1 | 10/2007 | Wehba et al. |
| 2007/0233281 A1 | 10/2007 | Wehba et al. |
| 2007/0233520 A1 | 10/2007 | Wehba et al. |
| 2007/0233521 A1 | 10/2007 | Wehba et al. |
| 2007/0273504 A1 | 11/2007 | Tran |
| 2007/0276270 A1 | 11/2007 | Tran |
| 2008/0000979 A1 | 1/2008 | Poisner |
| 2008/0086533 A1 | 4/2008 | Neuhauser et al. |
| 2008/0093447 A1 | 4/2008 | Johnson et al. |
| 2008/0114226 A1 | 5/2008 | Music et al. |
| 2008/0114490 A1 | 5/2008 | Jean-Pierre |
| 2008/0138604 A1 | 6/2008 | Kenney et al. |
| 2008/0140444 A1 | 6/2008 | Karkanias et al. |
| 2008/0162192 A1 | 7/2008 | Vonk et al. |
| 2008/0178126 A1 | 7/2008 | Beeck et al. |
| 2008/0201174 A1 * | 8/2008 | Ramasubramanian ................ G16H 20/10 705/3 |
| 2008/0219493 A1 | 9/2008 | Tadmor |
| 2008/0275738 A1 | 11/2008 | Shillingburg |
| 2008/0279420 A1 | 11/2008 | Masticola et al. |
| 2008/0281630 A1 | 11/2008 | Sekura |
| 2008/0290168 A1 | 11/2008 | Sullivan et al. |
| 2008/0297589 A1 | 12/2008 | Kurtz et al. |
| 2008/0303638 A1 | 12/2008 | Nguyen et al. |
| 2009/0012818 A1 | 1/2009 | Rodgers |
| 2009/0018867 A1 | 1/2009 | Reiner |
| 2009/0043610 A1 | 2/2009 | Nadas et al. |
| 2009/0048871 A1 | 2/2009 | Skomra |
| 2009/0062624 A1 * | 3/2009 | Neville .................. G16H 50/20 600/300 |
| 2009/0095837 A1 | 4/2009 | Lindgren |
| 2009/0128330 A1 | 5/2009 | Monroe |
| 2009/0149721 A1 | 6/2009 | Yang |
| 2009/0159714 A1 | 6/2009 | Coyne, III et al. |
| 2009/0217194 A1 | 8/2009 | Martin et al. |
| 2009/0245655 A1 | 10/2009 | Matsuzaka |
| 2010/0042430 A1 | 2/2010 | Bartfeld |
| 2010/0050134 A1 | 2/2010 | Clarkson |
| 2010/0057646 A1 | 3/2010 | Martin et al. |
| 2010/0092093 A1 | 4/2010 | Akatsuka et al. |
| 2010/0136509 A1 | 6/2010 | Mejer et al. |
| 2010/0138154 A1 | 6/2010 | Kon |
| 2010/0255598 A1 | 10/2010 | Melker |
| 2010/0262436 A1 | 10/2010 | Chen et al. |
| 2010/0316979 A1 | 12/2010 | Von Bismarck |
| 2011/0021952 A1 | 1/2011 | Vallone |
| 2011/0082712 A1 | 4/2011 | Eberhardt |
| 2011/0119073 A1 | 5/2011 | Hanina et al. |

(56) References Cited

U.S. PATENT DOCUMENTS

| | | | |
|---|---|---|---|
| 2011/0153360 | A1 | 6/2011 | Hanina et al. |
| 2011/0161109 | A1 | 6/2011 | Pinsonneault et al. |
| 2011/0195520 | A1 | 8/2011 | Leider et al. |
| 2011/0275051 | A1 | 11/2011 | Hanina et al. |
| 2012/0009555 | A1* | 1/2012 | Hanina ............ G16H 40/63 434/262 |
| 2012/0075464 | A1 | 3/2012 | Derenne et al. |
| 2012/0121729 | A1* | 5/2012 | Paterson ............ A61P 29/00 424/670 |
| 2012/0316897 | A1* | 12/2012 | Hanina ............ G16H 20/70 705/3 |
| 2013/0044196 | A1 | 2/2013 | Gualn et al. |
| 2014/0184772 | A1* | 7/2014 | Hanina ............ H04N 7/18 348/77 |
| 2014/0376876 | A1* | 12/2014 | Bentley ............ G06K 9/00744 386/227 |

FOREIGN PATENT DOCUMENTS

| | | |
|---|---|---|
| WO | WO 2011/062934 | 5/2011 |
| WO | WO 2012/177524 | 12/2012 |
| WO | WO 2014/152828 | 9/2014 |

OTHER PUBLICATIONS

Ammouri and Biloduau, *Face and Hands Detection and Tracking Applied to the Monitoring of Medication Intake*, Computer and Robot Vision, 2008. CRV '08. Canadian Conference pp. 147-154, (May 28-30, 2008).

Batz, et al. *A computer Vision System for Monitoring Medication Intake*, in Proc. IEEE 2nd Canadian Conf. on Computer and Robot Vision, Victoria, BC, Canada, (2005) (8 pages).

Bilodeau et al. *Monitoring of Medication Intake Using a Camera System*, Journal of Medical Systems, [retrieved on Feb. 18, 2013] Retrieved from ProQuest Technology Collection (2011) (13 pages).

Chen, Pauline W., *Texting as a Health Tool for Teenagers*, The New York Times, Nov. 5, 2009, http://www.nytimes.com/2009/11/05/health/05chen.html?_r=1&emc (3 pages).

CN Office Action for CN App No. 201480014372.8 dated Aug. 2, 2018 (with English translation) (21 pages).

CN Office Action for CN App. No. 2014800143728, dated Jul. 31, 2017 (9 pages).

Danya International Inc., *Pilot Study Using Cell Phones for Mobile Direct Observation Treatment to Monitor Medication Compliance of TB Patients*, Mar. 20, 2009, www.danya.com/MDOT.asp (2 pages).

EP Supplementary European Search Report for EP 14770974, dated Aug. 22, 2016 (2 pages).

Huynh et al., *Real time detection, tracking and recognition of medication intake* World Academy of Science, Engineering and Technology 60: 280-287 (2009).

International Search Report in PCT/US14/27901, dated Aug. 19, 2014, p. 1-9.

Mintchell, *Exploring the Limits of Machine Vision*, Automating World, (Oct. 1, 2011) (6 pages).

Niebles, et al., *Unsupervised Learning of Human Action Categories Using Spatial-Temporal Words*, Int J Comput Vis. (Mar. 16, 2007) (20 pages).

Ostergerg and Blaschke, *Adherence to Medication*, New England Journal of Medicine 353:487-97 (Aug. 4, 2005).

University of Texas, *GuideView: When the physician is really far away*, Mar. 15, 2007, http://www.sahs.uth.tmc.edu/MSriram/GuideView (3 pages).

Valin, et al. *Video Surveillance of Medication intake*, Int. Conf. of the IEEE Engineering in Medicine and Biology Society, New York City, USA, Aug. 2006 (4 pages).

Wang et al. *Recent Developments in human motion analysis* Pattern Recognition 36: 585-601 (2003).

Whitecup, Morris S., *2008 Patient Adherence Update: New Approaches for Success*, Guideline Trend Report, Oct. 2008 (17 pages).

Wikipedia, *Super-Resolution*, (Oct. 5, 2010) (4 pages).

World Health Organization, *Global Tuberculosis Control: A short update to the 2009 report*, (2009) (48 pages).

Extended European Search Report in EP Appln. No. 18858751, dated Sep. 9, 2020, 6 pages.

\* cited by examiner

| Usability | Missing information | Suspicious | Cheating |
|---|---|---|---|
| MNV > 20 seconds | MNV in (PIM, EUT) | HTM in (PIM, end] | Pill detection after EM |
| TOT > 20 seconds | Too dark or too bright | MNV in (PIM, EUT) + no drinking | Pill detection after PIM + spitting |
| Opaque container | Corrupt video / missing frames | MNV in (PIM, EUT) + phone rotating | Pill detection after PIM + not swallowing |
| Phone rotating | | Not drinking + large pill | Miming PIH |
| Time out | | Spitting (with no pill detection) | Generic PIH fires and PIH doesn't |
| | | Not swallowing | Generic PIM fires and PIM doesn't |
| | | Close mouth between EM and EUT. | Wrong person |
| | | Short time PIM->EM | Double enrolment |
| | | | Not same pill for PIH or PIM |

Figure 3

RECOGNITION OF SUSPICIOUS ACTIVITIES IN MEDICATION ADMINISTRATION

CROSS-REFERENCE TO RELATED APPLICATION

This application claims priority to U.S. Provisional Application Ser. No. 62/560,528, filed on Sep. 19, 2017. The disclosure of the prior application is considered part of and is incorporated by reference in the disclosure of this application.

FIELD

The subject matter described in this application generally relates to patient compliance to medication administration protocol scenarios including ingestion of medication, and more particularly to an apparatus and method for the identification of suspicious or purposefully malicious activity on the part of the patient, where the patient is purposefully not properly administering their medication.

BACKGROUND

Traditionally, participants attend introductions and follow ups for clinical trials in-person. Other patients outside of the clinical trial setting attempting to adhere to a particular medication protocol similarly are given a prescription and a particular set of instructions from a prescribing medical provider or prescribing doctor. Compliance is then measured at a next visit with that prescribing professional through traditional methods of counting unused medication, and patient interviews. Thus, data collection is similarly limited to patient visits, rather than on a daily basis. These old methods such as patient questioning and medication counting have been proven to be inadequate measures of adherence and offer no information on dose timing and drug holidays (omission of medication for three or more sequential days).

SUMMARY

U.S. patent application Ser. No. 13/831,555, filed Mar. 14, 2013, titled Apparatus and Method for Recognition of Suspicious Activities to Hanina et al., the contents of this application being incorporated herein by reference in its entirety, describes a system, method and apparatus that allow for determination of suspicious activity by a patient administering medication following a predetermined protocol or prescription.

The subject matter described in this application is directed to a system and method for detecting suspicious activity of a user (hereafter also referred to as a patient), and to thwart users who purposefully do not take their medication. The system presents an advanced mechanism for teaching a system to acquire and learn what to look for related to suspicious activity, and further includes a mechanism for analyzing input captured video to determine suspicious activity. The system may also interact in real-time with the patient when something is identified as incorrect, wrong or suspicious and either prompt a different action or raise an alert and recommend an intervention by a healthcare provider.

In accordance with an embodiment of the subject matter described in the present application, a motion capture procedure for capturing patient motion data related to the administration of pill or film based oral medications, or injectable, inhaler-based, other non-pill based medication, or any other form of patient administration task that may be performed, may be utilized. Other capture sensors may further be utilized, including range (depth) sensors, hyperspectral sensors, such as infrared or near infrared sensor, and the like. Such sensors may help to localize and segment the face and hand, improving the ability to discern motion and other attributes of a video and other data capture. Use of such other sensors may also help to identify material properties of an item, such as a medication pill, thus assisting in confirming the pill's authenticity. Therefore, in accordance with an embodiment of the present application, a method and apparatus may be provided for analyzing the captured patient motion data to provide feedback to the user and/or to determine a number of times the user performs a suspicious action. The system can detect suspicious action and provide feedback to the user in near real-time, and importantly, in time sufficient to allow for the feedback to be useful to the subject while the subject is still performing the activity. Additionally, the patient performance information may be analyzed asynchronously to determine other features of data that may suggest a malicious intent on the part of the patient.

Still other objects and advantages of the subject matter described in this application will in part be obvious and will in part be apparent from the specification and drawings.

The subject matter described in this application accordingly comprises the several steps and the relation of one or more of such steps with respect to each of the others, and the apparatus embodying features of construction, combinations of elements and arrangement of parts that are adapted to affect such steps, all as exemplified in the following detailed disclosure, and the scope of the subject matter described herein will be indicated in the claims.

BRIEF DESCRIPTION OF THE DRAWINGS

For a more complete understanding of the subject matter described in this application, reference is made to the following description and accompanying drawings, in which:

FIG. 3 is a table describing monitored elements for determining one or more actions;

DETAILED DESCRIPTION

Compliance and medication adherence technologies can increase the statistical power of clinical trials. Through the use of such technology, clinical events can be precisely linked to medication use history. Captured data can be linked to other sources such as EDC, patient diaries and data collected by the physician. Technologies can create many possibilities for remote visits and data capture. While smart packaging technologies exist such as RFID-enabled computer chip technology, smart blister packs and MEMS caps (microprocessor in a bottle cap), they are: a) invasive and need to be physically attached to the medications; b) are non-conclusive regarding compliance—a patient may activate the technology without ingestion of the medication; c) remain largely un-adopted in clinical trials by the pharmaceutical and biotech companies due to their high cost; and d) take a longer time to implement. Further, electronic patient diaries allow for ease of entry of data by a patient. These diaries, however, are still subject to issues related to compliance with medication adherence. Thus, even if a patient is meticulous about entering information into the diary, and thus complying with the requirements for data entry, there is still no guarantee that they are properly taking medication at prescribed times. This problem is even more acute when a participant is performing a suspicious action, or is otherwise maliciously avoiding taking their medication.

Figure 1:
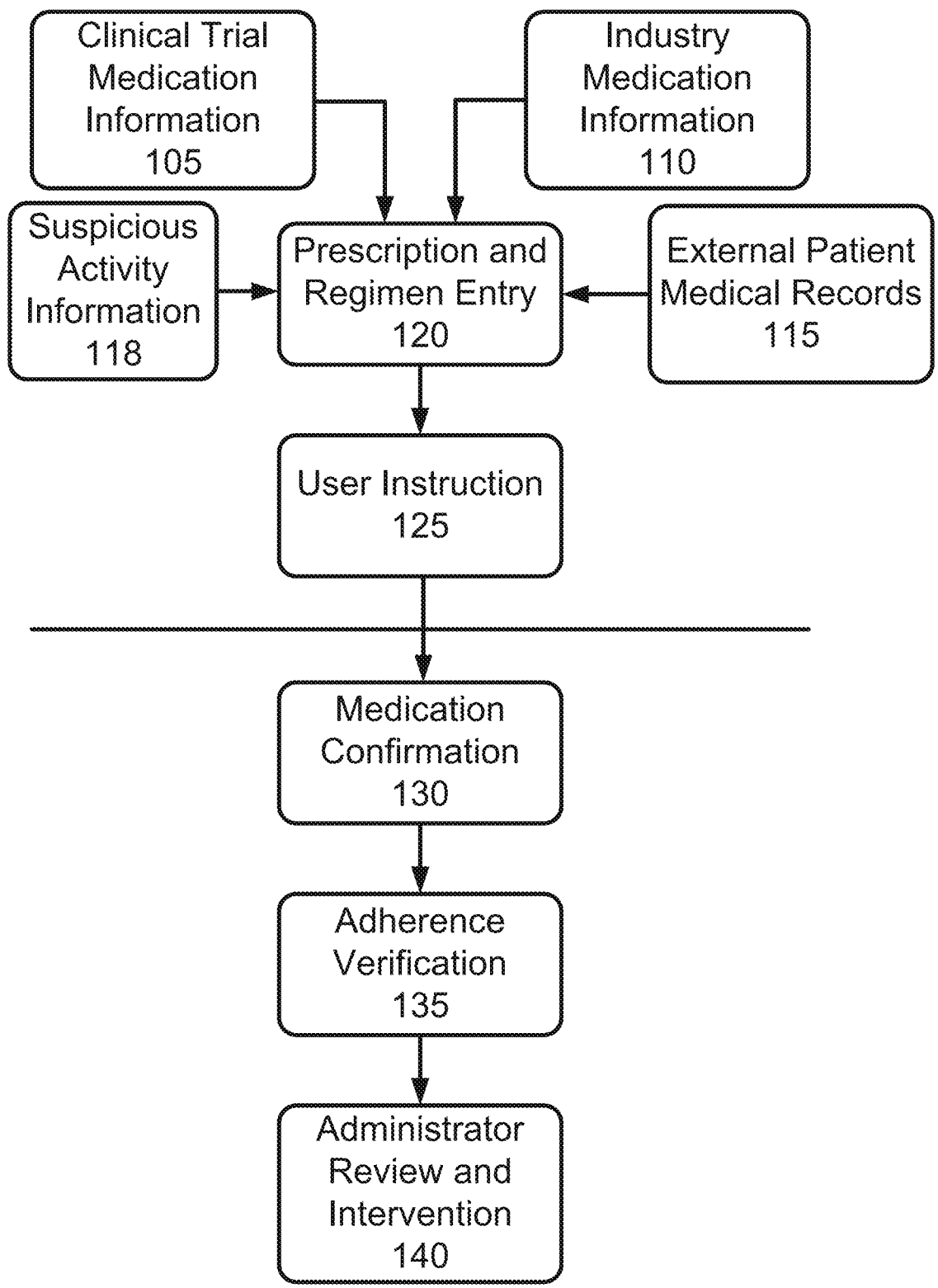
FIG. 1 is a flow chart diagram depicting a method for identifying suspicious activities of a patient administering a medication.

The subject matter of the present disclosure aims to address the drawbacks of the prior systems. The subject matter of the present disclosure will now be described making reference to the following drawings in which like reference numbers denote like structure or steps. Referring to FIG. 1, a data flow overview in accordance with the operation of a system (for example, the information capture and analysis system described in detail below with reference to FIG. 6 and FIG. 7) for identifying suspicious activities of a patient when administering a medication is shown. In accordance with this embodiment, information about a particular drug to be the subject of a clinical trial, to be employed in a public health or disease management situation, or the like, other medication administration program or prescription, or other patient self-administered medical task such as performing a home based urine test or the like may be provided in a hardware-based database 105. Existing industry medication information databases 110 are employed to access prescription, interaction, application, and other available information about any number of proposed prescription and non-prescription medications and their possible interaction with the clinical trial or other medications. Further, external patient medical records 115 may be used, and as will be described below, in conjunction with the industry medical information and a medical professional's prescribing expertise to confirm that a patient is a good candidate for such a clinical trial, or medication administration program. These databases may be accessed using non-manual techniques in a manner known to one of ordinary skill in the art. This information may further include information related to typical elements of suspicious or malicious behavior. Such elements may be based upon the type of medication, method of medication administration, demographics or other information about the patient, other features, or a combination of these elements. Suspicious activity information 118 is transferred to the system at this time as well, and as noted above may include one or more indications of patient movements or other actions that may indicate suspicious behavior on behalf of the patient, a malicious intent to trick the system, or actions of other high risk population. The various embodiments of the present invention may also be provided to determine if a patient is performing an action or task correctly or if they are simply making a mistake.

Once confirmed, a medication administration and ingestion or other medication regimen in accordance with the clinical trial or other prescription requirements such as in a public health, medical practice environment or the like may be prescribed and entered into the system of the invention at 120. Such medication administration regimen may include one or more of ingesting or swallowing a pill, using an inhaler device, using an injectable medication device, employing a patch, sublingual administration, a cheek or other skin located medication administration device or the like. Of course, the present invention may be applied to any patient administered procedure. Once entered into the system, a particular prescription regimen may cause a set of user instructions, various training sequences and the like 125 to be generated and transmitted to an apparatus (e.g., the remote information capture apparatus 1000 of FIG. 6) provided to a patient in accordance with an embodiment of the disclosure for access to the system. In accordance with an embodiment of the disclosure, instructions to be provided by the system (i.e., instructions to be displayed on an apparatus such as the apparatus 1000 of FIG. 6 and FIG. 7) to the patient are predefined for each different prescription for which the system is to be applicable. Thus, a healthcare provider, patient, or other individual may indicate the medication regimen to be administered by the patient to the system. In response, the system may provide a regimen (i.e. one pill, twice per day, etc.) to be followed by the patient. Similarly, if the medication to be administered is oral, training instructions and patient guidance for oral medication administration may be provided, while if other routes of administration are to be used, instructions for these routes may be provided. Finally, training modules may be available for additional modules to be provided, such as a barcode reading module, questions to be presented to and answered by the subject, etc. In this manner, once the patient is assigned a protocol, all required regimens, training materials and interaction materials will be provided to the patient to allow for automated, proper training and administration assistance for the assigned protocol.

Such an apparatus may comprise a user device, such as a smart phone, a netbook, a laptop computer, a desktop computer, a tablet device, a free standing or built into a mirror or cabinet, or other computing appliance. The apparatus includes a video and audio capture apparatus (e.g., a camera, a voice recorder, and/or a video capture device), and a video and audio analysis and transmission apparatus for transmitting the captured video/audio to another system or device. The apparatus allows for the display of the user instructions to a patient, and allowing for the eventual capture, analysis and transmission of video, audio and other analysis information. The apparatus can be considered as the patient facing portion of the system (e.g., the information capture and analysis system of FIG. 6). Once the patient is registered with the system, the patient can download and install a software application directed to a medication protocol on the apparatus. The software runs on the apparatus (local user device) asynchronous to a back end system (e.g., the remote data and computing device 3000). When the patient interacts with the software application, user information and data captured by the apparatus is encrypted, stored, and transmitted to a back end system. User information and data may be deleted after use. Separate software runs on the back end system can perform additional analysis to determine suspicious activities of the patient over time, for example, and then providing data/information about the suspicious activities to a healthcare provider on browser-based dashboards.

When installing software on a user's own hardware system, it is preferred that the software detect and otherwise test or determine that the hardware attempting to be utilized by the patient is sufficient to implement the system and method described in this disclosure and is sufficient to run a software package provided in accordance with the system and method described herein. Thus, the software may check that a camera includes sufficient resolution, that a memory of the device is of sufficient size to allow for sufficient captured video storage, that audio may be properly captured, and that the transmission system includes sufficient bandwidth to transmit and receive captured video, audio, video instructions and the like. Processing may also be performed at a remote location, thus allowing the user to include a lighter application or the like on their local device. Alternatively, the user may employ the local device as a gateway only, all data being transmitted to a remote system (e.g., the remote data and computing device 3000 of FIG. 6 and FIG. 7) for processing, and receiving responses from the remote system as a result of such processing. Thus, a user may be able to dial up a video conference number, or otherwise interact with a remote site, such as by visiting a particular website or URL.

Such user instructions and training sequences may include general instructions about the particular medication subject to the current trial or medication administration protocol, methods for administration, warnings about side effects, and concerns about drug interactions with common substances or medications, or other medications prescribed to the patient by the system or by another medical service provider. It is contemplated in accordance with an embodiment of the invention that such set of user instructions may be interactive, allowing a user to view additional information about such instructions or prescriptions as desired. These instructions may comprise written, audio or video instructions provided to the user on a display of the user apparatus. It is further contemplated that such instructions may indicate one or more movement sequences to be associated with a corresponding one or more medication administration sequences. These instructions indicate proper and improper motions that may be taken by a patient for ingesting a pill, using an inhaler, using an injectable medication, and the like, and may indicate various motions that may or may not be performed by a user. In such a manner, the patient may be instructed to properly perform all requested actions, and avoid actions that may be indicative of a patient trying to trick the system.

In an alternative embodiment, it may be possible to particularly not describe to the patient the various suspicious behaviors that will be tracked in an attempt to monitor without notification of the unsuspecting malicious patient. These traps may be maintained and running in a background of the system. Thus, as will be described below, detection of one or more errors may generate real time displayed video and/or audio feedback to the patient in order to correct actions during the session during which they are taking the medication so that the current administration session is not lost and may still be a successful administration, while one or more other errors may be logged by the system but preferably provide no feedback to the patient, and thus may be accumulated and used to analyze patient actions without providing instructions and help to avoid being recognized by the system. After being recognized as performing undesirable actions a predefined number of times (for example, after three, five, ten, twelve, or twenty times), the user may be identified as one who should have heightened security applied. Thus, a user may be first started in a low level of observation. After a predetermined number of potentially suspicious actions are recognized, the user may be labeled as a user that is attempting to trick the system, or that is performing one or more suspicious acts, thus warranting a heightened level of security. Additional suspicion will surround review of all actions of the patient. After properly using the system correctly for another predetermined period of time, the heightened level of security may be removed. If on the other hand, suspicious activity continues, the user may be recommended to be removed from a clinical trial, or taken off a particular medication, for example.

In accordance with one or more embodiments of the present disclosure, one or more of these sets of motions or actions may include confirmation that a user has placed a pill in their mouth and has properly swallowed the pill correctly and has therefore ingested the medication properly through visual confirmation of location, confirmation that the user has properly used an inhaler device through visual confirmation of position and/or audio confirmation of actuation, confirmation that the user has properly used an injectable device through visual confirmation of position and/or audio confirmation of actuation, or the like.

Referring to the lower portion of FIG. 1, the horizontal line indicates a time for patient administration of medication. At such time, the user may be notified to take their medication through any desirable communication and notification system, including text messaging, email, telephone call, automated calendar reminder or the like. While not explicitly shown, first, the identity of a user may be confirmed through the use of a facial recognition sequence, other biometric identification sequence, voice recognition, other password identification system, or a combination thereof. Other features of use of the system, such as time to turn on or time to perform other tasks may be recorded to further aid in determining a consistent identity of a user of the system. The user may also be asked to say "hello" or some other word sequence to allow for audio recognition of the voice of the user. Upon recognition of the individual, the system may display user data including one or more data items regarding the individual. For example, the data items may include one or more of patient name, patient status, medication to be administered, or calendar indicating to the patient when medication has been administered and if any administration times have been missed. In some cases, the data may include a score indicative of a level of compliance of the individual with the medication protocol. Other metrics may also be tracked, for example, a metric indicating whether too many skips have been registered by a user, or whether too many self-reports that the user has taken their medication without the use of the automated system, each indicating a potentially suspicious activity. The user data may be stored at a remote location (e.g., a distributed database system) to aid in determining whether a particular user is registering at more than one site, with more than one device, and thus attempting to be paid twice for the trial. Such patients are unlikely to be interested in taking the medication at all. Additional attributes of a patient may also be stored in a centralized database or the like to potentially alert other clinical trials of potential offenders. Thus, one or more of a patient behavior profile, facial identification characteristics, voice recognition patterns, or a combination thereof, may allow one or more patients to be placed on a watch list or the like after having been identified as noncompliers. Thus, patients trying to get medication from multiple clinics, patients trying to sign up for multiple clinical trials, or patients trying to sign up at multiple sites in a single clinical trial may be recognized and determined before being able to be engaged at these other sites.

In some implementations, the system shall be able to learn the pattern of suspicious patients based on all data collected (such as number of misses, number of skips, manual ratios, time on tasks, number of usability errors, number of suspicious errors, study coordinator/sponsors notes, flags, video reviewing results.). The system can learn the pattern using machine learning techniques such as unsupervised learning or supervised learning techniques, and therefore the system learns as data is processed during use. Based on prior patient data, the system is able to recognize patterns and classify the patient based upon these patterns. For example, if a patient is showing erratic administration time and times on task, coupled with some administration misses, and one or more suspicious activity errors, the patient may be classified as one likely to be lost to follow up, and to purposefully not take medication. A patient can therefore be easily classified as suspicious level 1, level 2, or not by checking whether the patient fits in certain pattern. The system will keep learning each day when more data are gathered and more patients are enrolled. Thus, a more accurate placement of the user in a particular category or risk classification, as will be described below, can be more accurately determined. This risk category can then be used to define a level of observance and appropriate follow up for the particular category of patient.

Once identified and notified of a type of medication to be administered, the patient may show the system a medication (e.g., a pill or dissolvable film), administration apparatus (e.g., an inhaler, injectable apparatus, or other medication form such as a pill bottle) to confirm that the medication is correct. As shown in FIG. 1, at step 130, the system confirms that the medication shown by the patient is the currently prescribed medication for the patient through the use of text recognition, medication recognition, barcode or other code reading of one or more unique identifiers from the administration apparatus, pill bottle or the like, or other appropriate medication recognition scheme.

In addition to recognizing the pill or other medication, the system may track how patient holds the pill or other medication, and further may track continuous motion from hand to mouth to confirm that no suspicious action has taken place. Thus, the system may also check consistent hand usage between identification of the pill and placing the pill in the mouth of the user. In addition to tracking the motion of the hand, if the user is to take the pill out of a blister pack, the user may track a motion sequence for tracking complete gestures on screen from taking out of the pill bottle or blister pack all the way to placing in mouth/ingesting, drinking water, showing and tracking water go down, swallowing, and even showing empty mouth so that any deviation from the desired sequence may be identified as a potentially suspicious activity. Furthermore, the system may view the blister pack to determine if the correct number of pills have been removed, that the correct number of pills are remaining, and whether other pills or the like have been removed that should not have been removed. Such suspicious activity may be used to automatically flag potentially suspicious activity.

Thereafter, the system instructs the patient to administer the medication in the prescribed manner. One or more of these administration sequences may include confirmation that a user has placed a pill in their mouth (ingested the pill) through a visual confirmation of the location of the pill in the user's mouth, confirmation that the user has properly used an inhaler device through visual confirmation of position and/or audio confirmation of actuation, and/or confirmation that the user has properly used an injectable device through visual confirmation of position and/or audio confirmation of actuation.

The system (for example, the information capture and analysis system of FIG. 6) then verifies the patient's adherence to the prescribed administration schedule for the medication as prescribed by the clinical trial or other prescription regimen, while identifying suspicious or malicious behavior of the patient (step 135 of FIG. 1 for adherence verification). For example, for an oral administration, the system may ask the user to place the pill in their mouth, show the pill in their mouth to the camera to confirm its presence, drink a glass of water, and show an empty mouth to the camera to confirm the pill is gone. The system may ask the user to change the position of their tongue relative to the pill to provide a more complete view of the pill in the mouth of the user to the camera. For example, if the user only presents the top of their tongue to the camera, and refuses to show under their tongue, the system may flag that activity as suspicious. The system may further automatically recognize improper tilting of the glass of water, or the head of the user when drinking the water as potentially suspicious activity, and subsequently change the risk category of the user and/or change a level of scrutiny for reviewing activity of the user. The system may confirm swallowing motions, and identify the absence thereof as evidence of potentially suspicious or malicious behavior. For an inhaler, the system may ask the user to properly position the inhaler and show the positioning to the camera, to actuate the inhaler in view of the camera, to breathe in view of the camera, and to hold their breath for a predetermined period of time in front of the camera. The system may record and identify different sounds, for example different frequencies emitted from the inhaler, as suspicious given that, in some cases, the user may be blocking the aerosol or power of the inhaler with their teeth on purpose. Such incorrect positioning may suggest incorrect placement, and therefore incorrect medication administration. For an injectable medication, the system may ask the user to show the medication to the camera, to place the injectable medication adjacent the proper body part to receive the injection in view of the camera, to actuate the injectable medication in view of the camera, and the like.

During this administration, the system monitors potentially suspicious activities performed by the patient (step 140 of FIG. 1 for administrator review and intervention). In particular, the system may determine whether the head or face of the patient leaves the field of view of the camera may be determined, and as will be described below, a risk category of the user may be changed based upon this or other suspicious activities noted in accordance with this application. The system may track other suspicious activities including the patient covering their mouth with their hand during medication administration of a pill based medication and other body movements indicating an attempt to remove the medication or the like. Furthermore, the system may employ audio recognition to determine, for example, whether the patient is spitting out a pill, or to assist in determining whether an inhalable or injectable medication has been properly actuated. Each of these features may be preferably monitored over time so that while a single indication of potentially suspicious behavior provides important information, continued performance of such suspicious behavior will provide a more complete picture of attempts to trick the system, thus allowing for intervention to identify the patient, and address the suspicious behavior. Different actions performed on the part of the user may allow the user to be classified into one or more categories, the category being changed based upon one or more actions they may perform over time. Such a system may be provided in accordance with one or more features as described in copending U.S. patent application Ser. No. 13/189,518, filed Jul. 24, 2011 to Hanina et al., titled Method and Apparatus for Monitoring Medication Adherence, the contents thereof being incorporated by reference in its entirety. The medication administration system noted therein may be employed to classify suspicious users based upon their actions.

If a medication is being used to treat a certain symptom, therefore in accordance with one or more embodiments of the subject matter of this disclosure, the system may be employed to measure visually if that symptom is improving. For example, concentration, speed to complete tasks, motor control etc. If symptoms or behavior (eye movement still erratic for example) fail to improve, this may suggest that the user is not taking their medication. Mood may also be measured and monitored as a signal of whether the user is taking their medication. The system may perform various actions to classify a user in one or more medication administration risk category, thus suggesting a level of review and follow up that may be required by the system to follow up with the user.

Additionally, the system may determine a movement of the imaging device, through analysis of information provided in the field of view thereof, or through the use of one or more gyroscopes or accelerometers thereon. Thus, if the user tampers with the position of the imaging device or camera, the system can detect the user's suspicious action and automatically notifies a monitor or a healthcare provider. Other clues, such as changes in a background setting at one or more critical times of medication administration, or other indications of movement of the device, or the like.

After confirmation or failure of confirmation of such administration, the patient may be provided with a progress report regarding how they have performed over time, and further providing encouragement for future adherence. The progress report may include adherence to the medication protocol over time, adherence changes recently, percentage of medication protocol completed, etc. Additionally, notice of a next administration time may be provided, along with one or more messages from a healthcare provider regarding protocol changes, or other desired information. Furthermore, the system may report various detected instances of potentially suspicious behavior to a healthcare provider (e.g., a doctor or a nurse) via a dashboard, and preferably a browser-based dashboard that the healthcare provider can access over the Internet with a user name and password specific to the provider. The provider dashboard allows for the review of near real-time adherence and other information about each patient using the system. The dashboard reports general adherence information along with the noted suspicious activity information. The system may cause a display of a warning message to the patient. The warning message indicates that unusual activity has been detected. The warning message may inform the patient that incorrect use of the medication or protocol may result in their study coordinator/healthcare provider being contacted, their being removed from the trial, or there may be an additional level of monitoring applied to the patient.

Therefore, in accordance with the present disclosure, confirmation of patient adherence to the prescribed administration schedule for the medication as prescribed by the clinical trial or other prescription regimen may be determined by the system, which includes hardware component, while suspicious or malicious behavior may be identified by the system. While such confirmation may take a number of forms, in some embodiments, a method for such confirmation may include capturing a video and audio sequence of the patient actually administering the medication. In a further preferred method, such a sequence for such confirmation may include employing a facial recognition sequence or other biometric confirmation that a particular patient is in fact receiving treatment, but may also provide for the ability to obscure the face or other identifying feature of a user, simplify a displayed image through rotoscoping or the like, or otherwise encrypt such information to allow for the storage and use of such images while protecting the identity of the patient, a technique that may be beneficial when a medication administration manager is providing a general report about a clinical trial, and not trying to remedy a situation with a particular patient, or in particular in a public health or disease management scenario. Activity recognition, gesture recognition, computer vision processing, deep learning processing, or other feature for determining whether a particular subject movement meets a predefined movement sequence may be performed by a computer system to be sure that the patient is properly taking prescribed medication. This same gesture recognition may also be employed to determine suspicious or malicious behavior on the part of the user, as described above. Computerized techniques for performing activity recognition, gesture recognition are known in the art, for example, as described in Niebles, J. C., Wang, H., and Fei-Fei, L. *Unsupervised Learning of Human Action Categories Using Spatial-temporal Words*. Int J Comput Vis. 16 Mar. 2007. Audio recognition may also be employed by the system, which includes hardware components, to determine suspicious noises such as coughing noises or the like at one or more critical key moments associated with medication administration. For example, if coughing consistently occurs routinely after the user has pace a medication pill in their mouth, then the patient may be escalated to a risk category providing for a higher level of scrutiny of review during the administration process over time. Finally, measurement of time on task, indicative of an amount of time required for the user to perform one or more prescribed steps may also be employed by the system to aid in determining suspicious behavior. This time on task may be measured across many different devices and instances of use of the apparatus to determine one or more trends that may be interesting, and may be used to determine suspicious behavior. For example, time on task may be employed to determine miming of an activity that the user I not really performing the medication administration steps as required.

Figure 2:
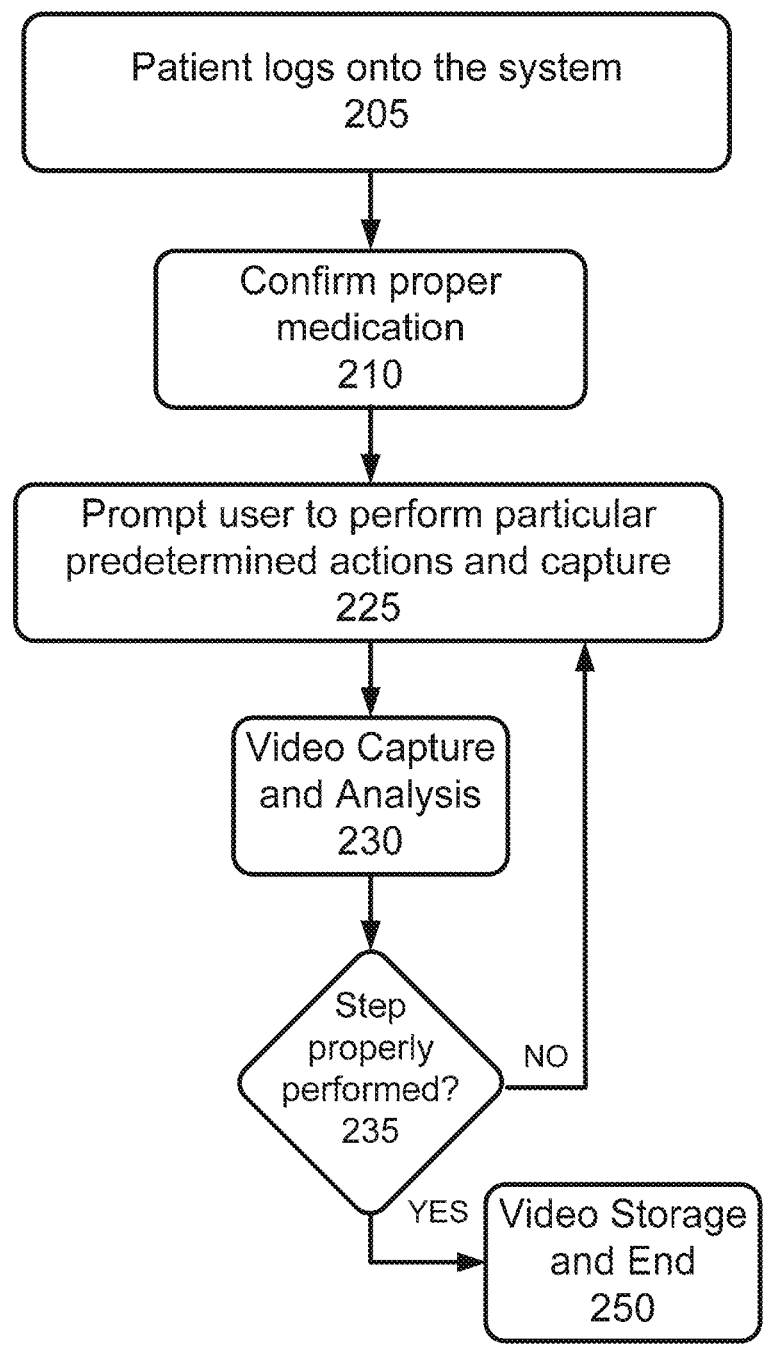
FIG. 2 is a flowchart diagram depicting a method for capturing a video sequence of a patient.

Referring next to FIG. 2, a method in accordance with an embodiment of the present disclosure for performing audio and video capture and recognition of adherence to a prescribed protocol, and for determining one or more indications of suspicious or malicious activities, is described, as set forth in steps 130 and 135 of FIG. 1. One or more of the steps of the method may be performed by the information capture and analysis system described in detailed below with reference to FIG. 6 and FIG. 7. In FIG. 2, a patient may first log into the system of the invention at step 205, employing the facial recognition, biometric recognition, password entry, voice recognition, or other patient identification method, and at step 210 proper medication is preferably confirmed as noted above, through the use of bar code reading, text recognition, visual recognition employing video or still image recognition, or other medication recognition technique as described above. The patient may be reminded to log onto the system to take their medication through any type of reminder, such as a text message, email, phone call, automated alarm or the like. Processing then passes to step 225 where the system prompts the user to perform one or more predetermined actions and captures the video and/or audio of each of these actions. The system analyzes the captured video/audio of each of these actions at step 230. At step 235, the system may determine whether the action has been properly captured, and whether the captured action has been properly analyzed by the system in one or more manners as will be described below. That is, the system checks to confirm whether the captured action has been properly captured, and whether the action has been properly analyzed. The failure of this step results in a request to recapture the information to re-perform the capture and analysis step.

If the system determines that administration of the medication did not take place properly, processing may return to step 225 and the user may be once again prompted to perform the action. (Of course, if this process involves actual administration of pill, film, inhaler, injectable medication, or any other medication, it may not be proper to request re-performance of the action, unless it can be determined that the user did not actually administer the medication.) If the action has been properly performed and is able to be analyzed, processing ends at step 250 where the various captured video sequences are stored. These stored sequences may also be made available for human review and involvement, when it is determined that this would be beneficial, and may further preferably be employed to determine suspicious or malicious activity. Areas of interest for review may be highlighted and marked as potentially including suspicious or incorrect activity. Percentage estimates of risk may be automatically provided by the system based on risk algorithms that are generated, and based upon a category into which the user may have been placed based upon their prior activity, and one or more learned activities from a plurality of users.

Figure 6:
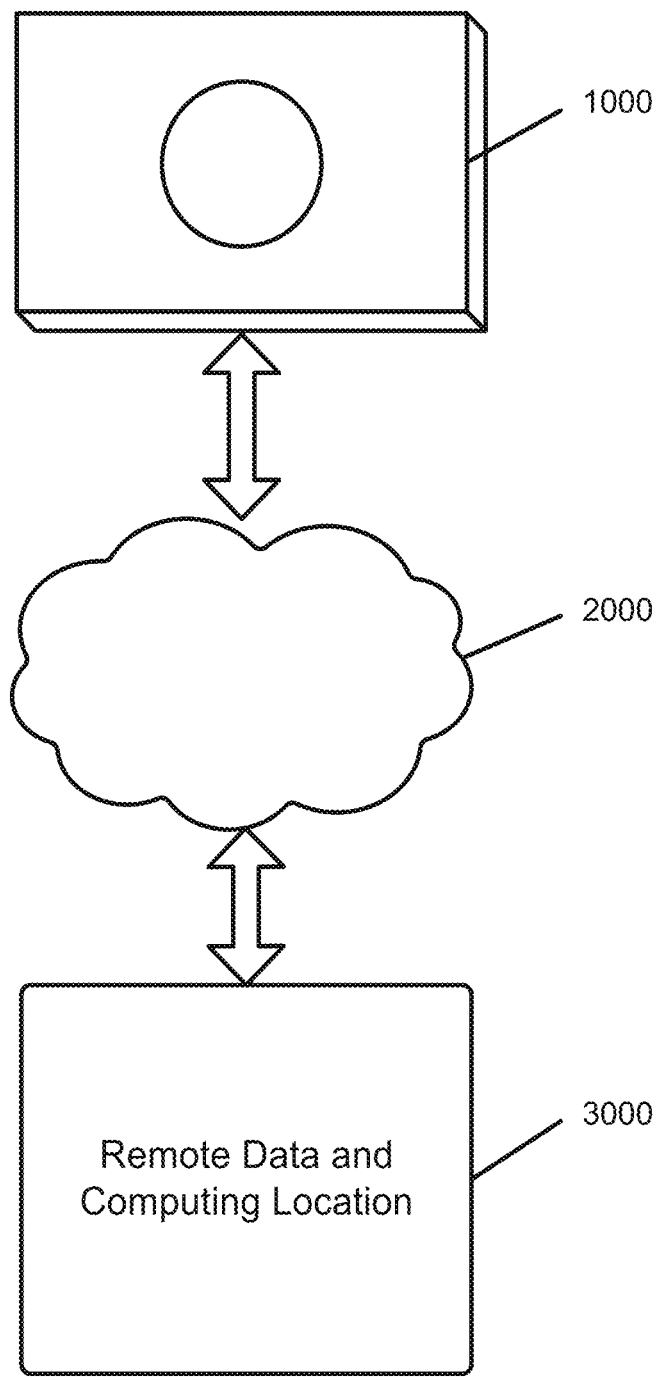
FIG. 6 is a block diagram depicting the details of an exemplary hardware configuration for implementing the system and method described in this application.

Referring next to FIG. 3, a table is shown describing a plurality of items to be monitored by a system such as the information capture and analysis system of FIG. 6 during medication administration (within the table), and a category for which the monitored item is applicable (noted across the top of the table on the first row). In some implementations, the table is stored in a database and the system can reference the database to determine which items to monitor. In some implementations, items to be monitored can be selected by an operator or user of the system ahead of time. Thus, in addition to monitoring items for suspicious activity, monitored items may also be used to monitor usability, suspicious activity, or cheating, or confirm that some information is missing. Please note that the following acronyms are used in FIG. 3: Mouth not Visible (MNV); Pill In Mouth (PIM); Empty Mouth (EM); Empty Under Tongue (EUT); Time On Task (TOT); Hand To Mouth (HTM); Same Not Same (SNS).

Thus, as is shown in FIG. 3, elements monitored for usability include 1) Mouth Not Visible; 2) Time on Task greater than 20 seconds; 3) Use of an opaque container; 4) Rotation of the mobile device; and 5) Time out of the system. Monitoring of these elements over time in accordance with the subject matter described in this disclosure will give a picture of status of the user related to usability issues.

Elements monitored for suspicious activity include: 1) Hand to Mouth (HTM) during or after the Pill in Mouth step; 2) Mouth not Visible (MNV) during or after the Pill in Mouth (PIM) Step, or when checking for an Empty space under the Tongue when not drinking; 3) Mouth not Visible during or after the Pill in Mouth Step, or when checking for an Empty space under the Tongue and the phone is rotating; 4) When the patient is not drinking and the pill is physically large, and thus hard to dry-swallow. More specifically, if the pill is very large/hard to swallow without liquid, and if the system determines that the patient nonetheless does not have any liquid, the system can determine that this is a suspicious activity; 5) if the patient is found to be spitting out the pill; 6) if the patient is found not to be swallowing; 7) if the patient is found to have a closed mouth between the empty mouth step and the empty under tongue check step; 8) if there is a very short time (e.g., one second or two seconds) between the pill in mouth and the empty mouth step (e.g., the time between the pill in mouth and the empty mouth is less than a predefined time); 9) if there is considerable motion from the muscles of mastication and buccinators (jaw and cheek). Considerable motion refers to motion that is sufficient for the system to determine that the user has placed the pill in their cheek. The system can learn to determine consideration motion over time when trained with examples of patients placing the pill in their cheek.

Elements monitored for cheating activity include: 1) Pill detection after empty mouth; 2) Pill detection after pill in mouth and spitting of the pill; 3) Pill detection after pill in mouth and detection of not swallowing; 4) Miming of the pill in hand step; 5) Generic pill or object in hand is confirmed, while the specific pill of interest in hand is not confirmed; 6) Generic pill or object in mouth is confirmed, while the specific pill of interest in mouth is not confirmed; 7) wrong person is recognized; 8) double enrollment is recognized; and 9) the pill recognized for the pill in hand and the pill in mouth steps do not match.

Finally, elements monitored to confirm missing information include: 1) mouth not visible in either of the pill in mouth or the empty under tongue check; 2) system recognizes it is too bright or too dark, and 3) there is corrupt video or missing frames.

The system may provide responses to the user in real time or near real time in the event that one or more of the elements to be monitored are recognized, thus providing immediate and helpful feedback to the user to properly perform the desired sequence of actions. As noted above, it may be desirable to not report some of the monitoring results to the user, so that a consistent review of action may be provided without alerting the user to adjust their behavior.

Figure 4:
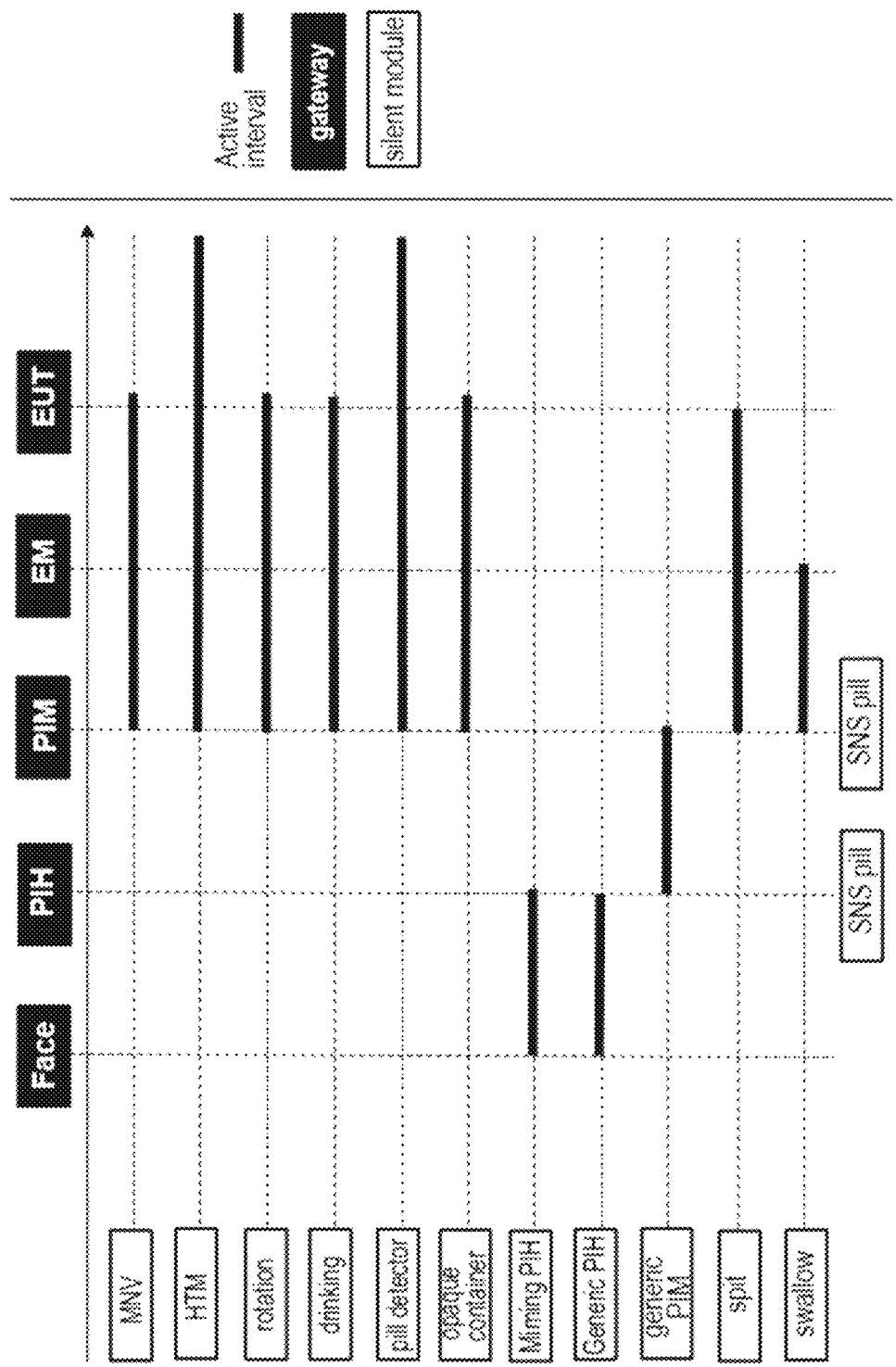
FIG. 4 is a timing chart depicting timing of monitoring of one or more items to be monitored.

As is next shown in FIG. 4, a chart is provided depicting steps (as noted above) related to confirming medication administration. In some implementations, the chart is stored in a database and the system can reference the database to determine which steps to be performed by the system. In some implementations, the steps to be performed by the system can be preset by an operator or user of the system ahead of time. These steps are noted in the top row in FIG. 4, which includes: 1) facial recognition (Face); 2) pill in hand (PIH) confirmation; 3) pill in mouth (PIM) recognition; 4) empty mouth (EM) check and empty under tongue (EUT) check. Additionally depicted are the elements to be monitored, including: 1) mouth not visible; 2) hand to mouth; 3) rotation of camera; 4) problems while drinking; 5) pill detector; 6) opaque container detector; 7) miming of pill in hand step (i.e., the system determines in advance there is no pill in the hand); 8) a generic pill (i.e., a pill that has been identified as not corresponding to the expected pill) used in the pill in hand step; 9) a generic pill used in the pill in mouth step; 10) recognition of spitting out of the pill; and 11) recognition of pill swallowing. The chart depicts during which steps associated with medication administration each of the measured elements are preferably monitored.

The left column and the bottom row of FIG. 4 use the following notations: PIH for pill in hand, PIM for pill in mouth, EM for empty mouth, EUT for empty under the tongue, MNV for mouth not visible, HTM for hand to mouth, SNS for Same/Not Same.

The top row of FIG. 4 represents steps performed by a patient (e.g., face confirmation, pill in hand, pill in mouth, empty mouth, and empty under tongue.) The left column notes types of motions or gestures of the patient that the system is configured to look for. Bar graphs in FIG. 4 shows during which steps the motions or gestures that the system is looking for are potentially "active."

During the "pill in hand" and "pill in mouth" steps (when a pill is visible), the system can also check whether the pill is still the same as originally imaged (to check for substitution).

In accordance with a further embodiment of the subject matter described in this disclosure, monitored elements may be combined in accordance with an equation of the Bayesian form as follows.

$$p[\text{cheating data}] \propto p[\text{data cheating}]p[\text{cheating}]$$

Figure 5:
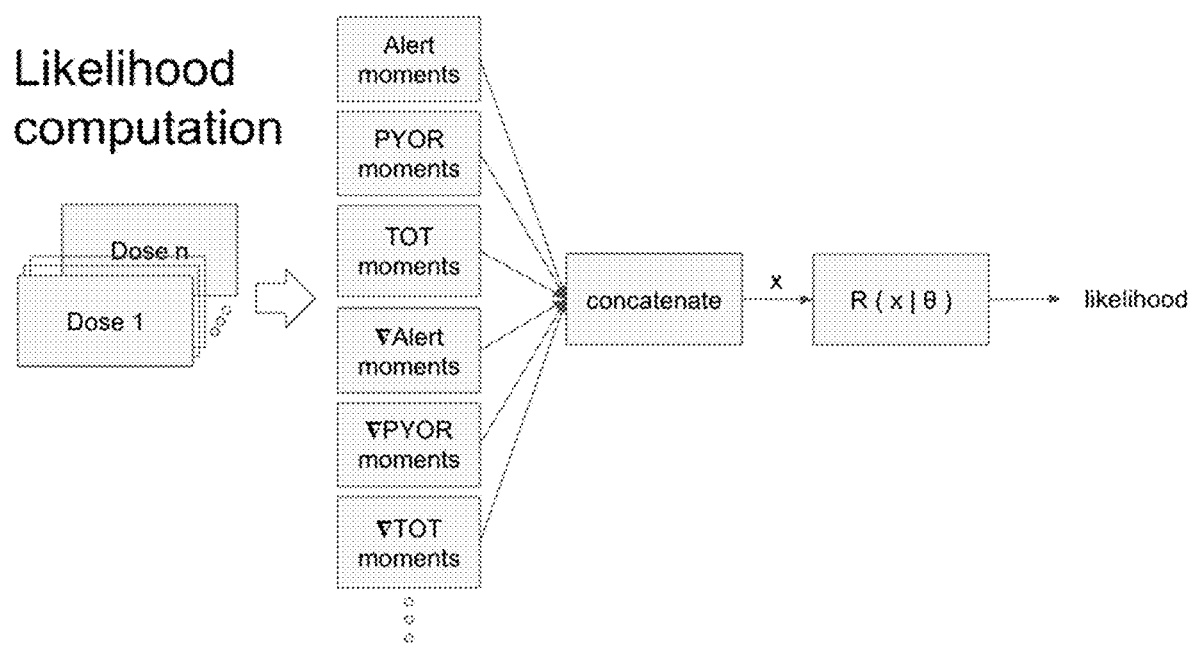
FIG. 5 is a depiction of a method for calculating a likelihood of cheating by a patient.

The equation notes that the probability of cheating being detected is proportional to the likelihood that the data will support an inference of cheating and a prior determination of the probability of cheating. The likelihood that the data will support an inference of cheating is preferably a concatenation of a number of elements, as shown in FIG. 5. Bayes formula (or other appropriate functions) can also be applied iteratively here to perform Bayesian updates of the posterior probability over time as we collect additional evidence. In the update step the posterior probability estimate from the previous timestep can be treated as the updated prior for the next timestep. In this manner, the estimation will gradually give more and more weight to the observed evidence and less weight to the initial a priori belief.

$R(x/\theta)$ is a regression model parameterized by theta which infers a continuous likelihood value based on the evidence x (concatenation of the features). $\Theta$ are the parameters of the model which can be modified over time. In particular, $\theta$ can be learned from supervised data. The training data, in accordance with an embodiment of the present disclosure, comprises videos of doses and their corresponding features x. Supervision of the training system and process comes from one or more other computer systems or human annotators and from PK data whenever that is available. Thus, confirmation of status of particular actions from one or more other computer systems or human annotators may be provided to the learning system at the time of acquisition or at a later date in order to teach the system preferred and proper evaluation, allowing the system to in the future also make such accurate and proper evaluations. Examples of implementations of R can be, Support Vector Regression, Random Forest, Logistic Regression, Neural networks, Recurrent neural networks, LSTMs, etc.

Calculation of the prior determination of the probability of cheating is preferably related to one or more of Age, Gender, Race, on any additional attribute found to be related to likelihood of cheating. These additional attributes may be determined in accordance with analysis of prior data related to medication administration and determined cheating. Data may furthermore be collected from one or more patient populations related to therapeutic area, response to medications, co-morbidities, other demographic information, and the like. Such data may also be provided by one or more healthcare providers, sites in clinical trials, or other available databases of information.

The system may provide one or more prompts to a patient related to measurement of any of the elements shown in FIG. 3 or 4. Prompts may be selectively provided to the patient, so that certain prompts encourage proper administration by the user, while other prompts may be withheld so that actions may be monitored without alerting the patient that their activity is under scrutiny.

Mechanisms for measuring the elements in FIG. 3 or 4 may be provided in an interactive manner as well. For example, if a patient is suspected of not properly administering their medication, the system may react adaptively to the actions of the patient, and for example, ask the patient to pull open their cheek or adjust the position of their open mouth to allow the camera to have a better view of the inside of the mouth of the patient to allow for a better chance to see if a pill is still positioned within the mouth of the patient. The system may further employ one or more 3D cameras, infrared cameras, or other cameras designed for a particular purpose in order to improve the quality of images and the ability to see, for example, distortion of the cheek of a patient attempting to hide a medication pill. The system may employ these additional video capture techniques, and may further provide feedback to the patient during medication administration, such as by requesting, for example, that the device be brought closer to the mouth of the patient to provide a better view thereof, by looking at one or more predetermine micro-expressions indicative of swallowing, attempts to hide the medication, pill, removal of the medication pill and the like. Audio recognition may also be used, either alone or in conjunction with the video capture, to further allow review of the system to, for example, listen for the sound of pills being spit out. Video capture may be performed at very high speed, allowing for subsequent higher temporal resolution review of elements of medication administration. Video element may also be amplified to allow for easier distinction of medication adherence issues. Additionally, the system may compare captured video information to previously captured video to look for anomalies, i.e. differences from standard performance of medication administration, or similarities to administration actions designated to be suspicious.

The system may further present one or more questions, or other information to the patient in response to a recognition of potentially suspicious activity, and gauge a response. The response can be considered for not only content, but also for status of the user when responding. Thus, it is possible to judge whether the user appears to be nervous and stressed or calm when answering the question, for example. Other issues, such a slurring speech, speeding up or slowing down when speaking may also be correlated with the responses from the user and ultimately correlating with an actual determination of whether the user is properly administering the medication, or is cheating/performing suspicious activity.

Users may be associated with a score indicative of medication adherence, likelihood of future proper medication adherence or the like. Through such a scoring system, it is possible to easily categorize and manage users so that similarly-scored users can be provided with similar intervention, follow up and scrutiny.

Deep learning and other supervised or unsupervised learning techniques may be employed to improve the responsiveness of the system, and to extract patterns that may be predictive of future action on the part of users. Thus, such expert systems may review input data in an automated fashion, and provide correlations between the data that are predictive in the future moving forward.

In a further embodiment, it is possible to provide a unique serialization of medication so that the system may confirm that each and every dose is correct. Thus, each bottle, or each dose, may be imprinted with a unique identifying barcode, QR code, data matrix code, or other code that allows for a reader to determine an identity based upon a visual capture of the code. Codes may be assigned to define categories of pills, individual groups of doses, or individual pills, and may further be customized to allow for the assignment of a particular pill to be correlated with a single individual. Thus, facial recognition results may be combined with QR code results from a bottle or pill to confirm that the correct pill is being taken by the corresponding correct person.

According to another aspect, once the analyses noted above have been performed, in order to encourage the system to learn more about human behavior, measurements of actual drug levels, for example, may be determined and fed back into the system. Therefore, by way of example, if during monitoring, the system finds a particular patient who have caused one or more of the elements for suspicious activity to have been recognized, subsequent to this process, the system may determine actual drug levels in the blood of the patients. This is an accurate depiction of whether the patient has ingested the medication, at least on the few days before the blood was drawn (depending on half-life of drug). Thus, it is possible to correlate recognition of suspicious activity elements (or other elements) with actual drug blood levels. The system may recognize patterns or groups of elements that correlate with lack of drug in the blood, and then use the patterns or groups of elements in the future to better predict the likely failure to properly administer medication. Furthermore, as additional information becomes available, such as in a clinical trial where it might be years before knowledge of actual medication blood levels may be determined, data may be reprocessed to determine any correlations between any one or more of the monitored elements and actual drug levels.

Therefore, in accordance with the present disclosure, a method and apparatus are provided that allow for the automated confirmation of adherence to administration protocol for medication, and provide for a most sophisticated method for confirming and studying methods of administration of such prescription medication. The system described in this disclosure can monitor suspicious activity, cheating, and other elements in order to insure proper administration, and can learn to improve its performance based upon actual use of the system by patients.

FIG. 6 illustrates an information capture and analysis system that includes a remote information capture apparatus 1000, a communication system 2000, and a remote data and computing device 3000. The information capture and analysis system is adapted to allow for the capture and processing of information in order to implement the system and method in accordance with the present disclosure. The information capture apparatus 1000 communicates with a remote data and computing device 3000 via a communication system 2000 (e.g., the Internet, Wi-Fi, LAN, WAN, Bluetooth, or other communication system). Via the communication system 2000, information captured by apparatus 1000 may be transmitted to remote data and computing device 3000, and analysis information or other instructions may be provided from remote data and computing device 3000 to apparatus 1000. It is further contemplated that a plurality of such information capture apparatuses 1000 may be coordinated to monitor a larger space than a space that can be covered by a single such apparatus. Thus, the apparatuses can be made aware of the presence of the other apparatuses, and may operate by transmitting all information to one of the apparatuses 1000, or these apparatuses may each independently communicate with remote data and computing location, which is adapted to piece together the various information received from the plurality of devices 1000.

Figure 7:
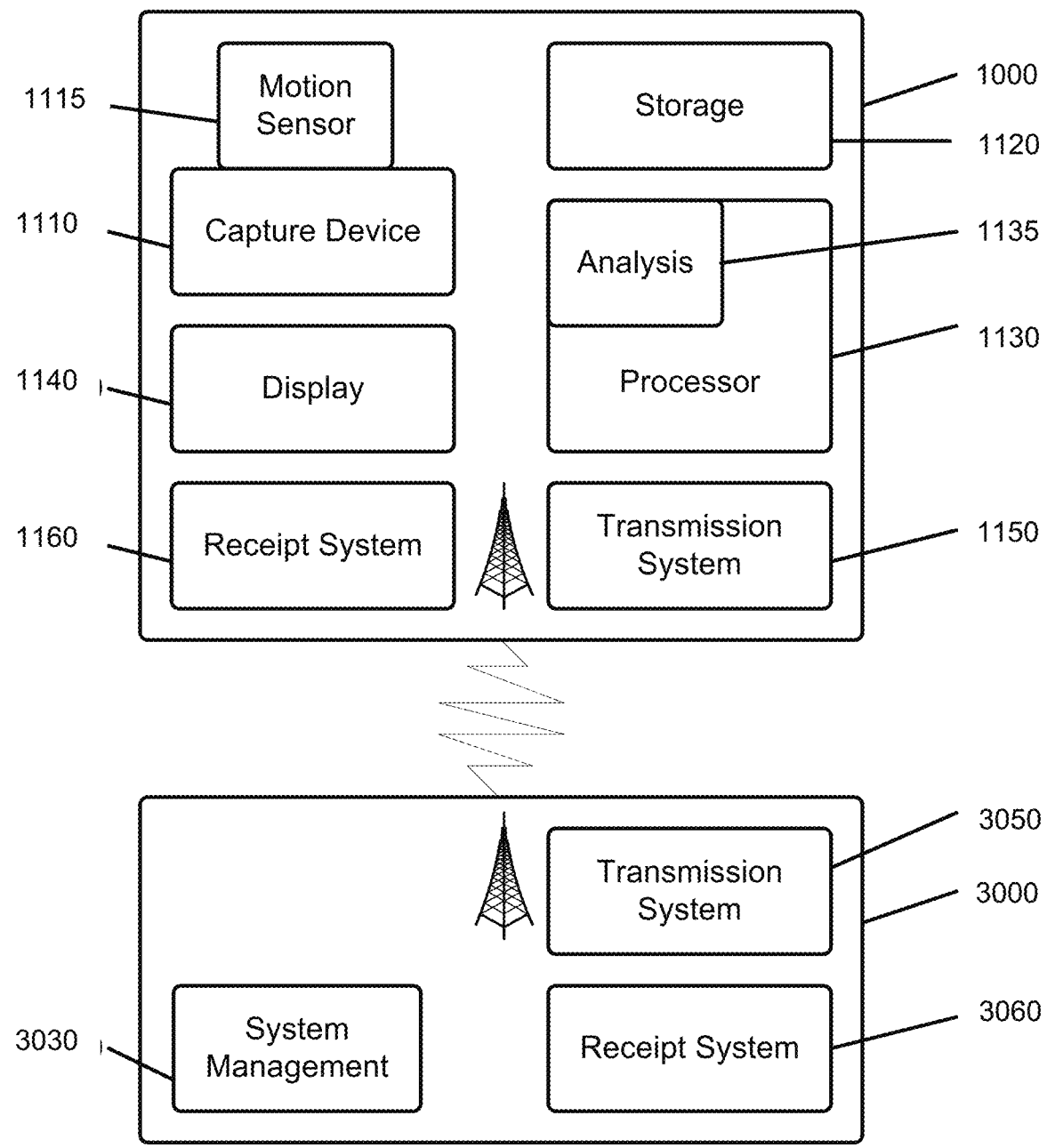
FIG. 7 is a block diagram depicting additional details of an exemplary hardware configuration for implementing the system and method described in this application.

FIG. 7 shows a more detailed view of an example embodiment of remote information capture apparatus 1000 and remote data and computing device 3000 of the information capture and analysis system of FIG. 6. As shown in FIG. 7, the apparatus 1000 comprises an information capture device 1110 for capturing video and audio data as desired. A motion detector 1115 or other appropriate trigger device may be provided associated with capture device 1110 to allow for the initiation and completion of data capture. Information capture device 1110 may comprise a visual data capture device, such as a visual camera, or may be provided with an infrared, night vision, or other appropriate information capture device. A storage location 1120 is further provided for storing captured information, and a processor 1130 is provided to control such capture and storage, as well as other functions associated with the operation of remote information capture apparatus 1000. An analysis module 1135 is provided in accordance with processor 1130 to perform a portion of analysis of any captured information at the remote information capture apparatus 1000. Apparatus 1000 is further provided with a display 1140, and a data transmission and receipt system 1150 and 1160 for displaying information, and for communicating with remote data and computing device 3000. In some embodiments, display 1140 may be used, along with an audio speaker, if desired, to provide one or more interview questions in accordance with an automated interview process. In such a situation, information capture device 1110 would then capture video and audio information provided by a user in response to the automated interview process.

The remote data and computing device 3000 comprises system management functions 3030, and a transmission and reception system 3050 and 3060 for communicating with apparatus 1000. Transmission and reception system 3050 and 3060 may further comprise various GPS modules so that a location of the device can be determined at any time, and may further allow for a message to be sent to one or more individual apparatuses, broadcast to all apparatuses in a particular trial, or being used for administration of a particular prescription regimen, of broadcast to all available apparatuses.

In accordance with an embodiment of the disclosure, apparatus 1000 is adapted to be part of a system that monitors user (patient) medication administration, and determined that the correct user is administering the correct medication at the correct time. Users of apparatus 1000 in accordance with this system give administrators a tangible and concrete manner in which to review activities and collected information related to proper medication administration. Apparatus 1000 of the disclosure is adapted to receive medication protocol and instructions for medication administration, or the like for patients from remote data and computing device 3000 and provide these instructions to patients to guide them in administering their medication. Such instructions may comprise written, audio or audio/video instructions for guiding a user to perform one or more medication administration activities, such as showing a face of the user, showing a pill to be ingested, or confirming that the medication has been properly ingested, and therefore confirming whether a user is adhering to a prescribed medication protocol. The video instructions can be provided either by a real person or by an animated cartoon character (avatar), or the like, and are designed to be interactive in nature.

It will thus be seen that the objects set forth above, among those made apparent from the preceding description, are efficiently attained and, because certain changes may be made in carrying out the above method and in the construction(s) set forth without departing from the spirit and scope of the subject matter described in this disclosure, it is intended that all matter contained in the above description and shown in the accompanying drawings shall be interpreted as illustrative and not in a limiting sense.

It is also to be understood that this description is intended to cover all of the generic and specific features of the subject matter described in this disclosure herein described and all statements of the scope of the subject matter described in this disclosure which, as a matter of language, might be said to fall there between.

Embodiments of the subject matter and the functional operations, for example, the computer system in FIG. 6 and FIG. 7 and the methods described in the detail above with reference to FIGS. 1-5, can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory program carrier for execution by, or to control the operation of, data processing apparatus. The computer storage medium can be a machine-readable storage device, a machine-readable storage substrate, a random or serial access memory device, or a combination of one or more of them.

The term "data processing apparatus" refers to data processing hardware and encompasses all kinds of apparatus, devices, and machines for processing data, including by way of example a programmable processor, a computer, or multiple processors or computers. The apparatus can also be or further include special purpose logic circuitry, e.g., an FPGA (field programmable gate array) or an ASIC (application-specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, a module, a software module, a script, or code, can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a data communication network.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application-specific integrated circuit).

Computers suitable for the execution of a computer program include, by way of example, can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface or a web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the user device, which acts as a client. Data generated at the user device, e.g., a result of the user interaction, can be received from the user device at the server.

While this specification contains many specific implementation details, these should not be construed as limitations on the scope of any subject matter described in this disclosure or on the scope of what may be claimed, but rather as descriptions of features that may be specific to particular embodiments of the subject matter described in this disclosure. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

The invention claimed is:

1. A system comprising one or more computers in one or more locations and one or more storage devices storing instructions that, when executed by the one or more computers, cause the one or more computers to perform operations comprising:
    analyzing a resolution of a video capture device of a user device;
    determining that the resolution of the video capture device satisfies a predetermined criteria;
    determining, based on analysis of a demographic population to which a user belongs, an initial determination of cheating probability; and
    performing a plurality of medication administration sessions, wherein performing each medication administration session comprises:
        displaying, by a display of the user device, one or more instructions directing the user to perform one or more predetermined actions to administer a medication,
        capturing, by the video capture device, one or more video sequences of the user administering the medication according to the one or more predetermined actions,
        analyzing the captured one or more video sequences to extract determinations of user behavior in a plurality of categories,
        calculating, based on the determinations of the user behavior and a user-specific prior determination of cheating probability, a cheating indicator, wherein the user-specific prior determination of cheating probability is based on the initial determination of cheating probability,
        updating the user-specific prior determination of cheating probability based on the cheating indicator indicating that the user is not properly administering the medication, wherein updating the user-specific prior determination of cheating probability results in de-weighting the initial determination of cheating probability in the user-specific prior determination of cheating probability, and
        adaptively performing a follow-up operation in response to the cheating indicator indicating that the user is not properly administering the medication.

2. The system of claim 1, wherein capturing the one or more video sequences of the user comprises:
    determining an identity of the user using one or more of the following methods: facial recognition, biometric recognition, password entry, or voice recognition.

3. The system of claim 1, wherein analyzing the captured one or more video sequences comprises:
    determining that the medication is a correct medication prescribed for the user based on one or more of text, a machine-readable code, or a unique identifier associated with the medication, wherein the determinations of the user behavior comprise the determination that the medication is the correct medication prescribed for the user.

4. The system of claim 1, wherein analyzing the captured one or more video sequences comprises:
    determining whether a sequence of user movements depicted in the one or more video sequences match a predefined movement sequence using an image processing technique.

5. The system of claim 1, wherein extracting the determinations of the user behavior in the plurality of categories comprises determining one or more of the following: 1) a hand of the user is at a mouth of the user during or after the medication is placed in the mouth, (2) the mouth is not visible during or after the medication is placed in the mouth, 3) the user is spitting out the medication, 4) the user is not swallowing the medication, 5) the user has a closed mouth between a time when the user empties the mouth after drinking the medication and a time when an under tongue area of the user is checked, 6) a time period between a time when the medication is in the mouth and a time when the user empties the mouth after drinking the medication is less than a predefined amount of time, or 7) a motion indicating that the user has placed the medication in their cheek.

6. The system of claim 1, wherein the operations comprise:
    determining whether at least one of the one or more video sequences has missing frames, wherein the cheating indicator is based on whether the at least one of the one or more video sequences has missing frames.

7. The system of claim 1, wherein adaptively performing the follow-up operation comprises:
displaying, by the display, a warning message to the user, the warning message indicating that one or more indications of cheating activity have been determined.

8. The system of claim 1, wherein adaptively performing the follow-up operation comprises:
causing a presentation of one or more follow-up questions to the user; and
evaluating behavior of the user when responding to the one or more follow-up questions to determine whether the user is cheating.

9. The system of claim 1, wherein adaptively performing the follow-up operation comprises:
requesting, by the display, the user to adjust a position of a mouth of the user or to bring the video capture device closer to the mouth to provide a better view of the mouth.

10. The system of claim 1, wherein adaptively performing the follow-up operation comprises:
notifying a healthcare provider that one or more indications of cheating activity of the user have been determined.

11. The system of claim 1, wherein the cheating indicator comprises a Bayesian probability.

12. The system of claim 1, wherein the operations comprise:
subsequent to capturing the one or more video sequences of the user administering the medication, obtaining blood test data of the user;
determining a correlation between the user behavior in the plurality of categories in the one or more video sequences and a level of the medication in blood of the user based on the blood test data; and
calculating a subsequent cheating indicator based on the correlation between the user behavior and the level of the medication in the blood.

13. The system of claim 1, wherein calculating the cheating indicator comprises:
calculating the cheating indicator based on corrupt video in the one or more video sequences.

14. The system of claim 1, wherein the user behavior comprises:
drinking or lack of drinking of a liquid in comparison to a size of the medication.

15. The system of claim 1, wherein the user behavior comprises:
whether a first medication held in a hand of the user matches a second medication in a mouth of the user.

16. The system of claim 1, wherein calculating the cheating indicator comprises:
calculating the cheating indicator based on a regression model, and
wherein the operations comprise:
modifying parameters of the regression model based on supervised dosing data.

17. A computer-implemented method comprising:
analyzing a resolution of a video capture device of a user device;
determining that the resolution of the video capture device satisfies a predetermined criteria;
determining, based on analysis of a demographic population to which a user belongs, an initial determination of cheating probability; and
performing a plurality of medication administration sessions, wherein performing each medication administration session comprises:
displaying, by a display of the user device, one or more instructions directing the user to perform one or more predetermined actions to administer a medication,
capturing, by the video capture device, one or more video sequences of the user administering the medication according to the one or more predetermined actions,
analyzing the captured one or more video sequences to extract determinations of user behavior in a plurality of categories,
calculating, based on the determinations of the user behavior and a user-specific prior determination of cheating probability, a cheating indicator, wherein the user-specific prior determination of cheating probability is based on the initial determination of cheating probability,
updating the user-specific prior determination of cheating probability based on the cheating indicator indicating that the user is not properly administering the medication, wherein updating the user-specific prior determination of cheating probability results in de-weighting the initial determination of cheating probability in the user-specific prior determination of cheating probability, and
adaptively performing a follow-up operation in response to the cheating indicator indicating that the user is not properly administering the medication.

18. The method of claim 17, wherein capturing the one or more video sequences of the user comprises:
determining an identity of the user using one or more of the following methods: facial recognition, biometric recognition, password entry, or voice recognition.

19. The method of claim 17, wherein analyzing the captured one or more video sequences comprises:
determining that the medication is a correct medication prescribed for the user based on one or more of text, a machine-readable code, or a unique identifier associated with the medication, wherein the determinations of the user behavior comprise the determination that the medication is the correct medication prescribed for the user.

20. The method of claim 17, wherein analyzing the captured one or more video sequences comprises:
determining whether a sequence of user movements depicted in the one or more video sequences match a predefined movement sequence using an image processing technique.

21. The method of claim 17, wherein extracting the determinations of the user behavior in the plurality of categories comprises determining one or more of the following: 1) a hand of the user is at a mouth of the user during or after the medication is placed in the mouth, (2) the mouth is not visible during or after the medication is placed in the mouth, 3) the user is spitting out the medication, 4) the user is not swallowing the medication, 5) the user has a closed mouth between a time when the user empties the mouth after drinking the medication and a time when an under tongue area of the user is checked, 6) a time period between a time when the medication is in the mouth and a time when the user empties the mouth after drinking the medication is less than a predefined amount of time, or 7) a motion indicating that the user has placed the medication in their cheek.

22. The method of claim 17, comprising determining whether at least one of the one or more video sequences has missing frames, wherein the cheating indicator is based on whether the at least one of the one or more video sequences has missing frames.

23. The method of claim 17, wherein adaptively performing the follow-up operation comprises:
displaying, by the display, a warning message to the user, the warning message indicating that one or more indications of cheating activity have been determined.

24. The method of claim 17, wherein the one or more video sequences are captured by an image capturing device, and wherein adaptively performing the follow-up operation comprises:
requesting the user to adjust a position of a mouth of the user or to bring the image capturing device closer to the mouth to provide a better view of the mouth.

25. The method of claim 17, wherein adaptively performing the follow-up operation comprises:
requesting, by the display, the user to adjust a position of a mouth of the user or to bring the video capture device closer to the mouth to provide a better view of the mouth.

26. One or more non-transitory computer-readable media storing instructions that, when executed by one or more computers, cause the one or more computers to perform operations comprising:
analyzing a resolution of a video capture device of a user device;
determining that the resolution of the video capture device satisfies a predetermined criteria;
determining, based on analysis of a demographic population to which a user belongs, an initial determination of cheating probability; and
performing a plurality of medication administration sessions, wherein performing each medication administration session comprises:
displaying, by a display of the user device, one or more instructions directing the user to perform one or more predetermined actions to administer a medication,
capturing, by the video capture device, one or more video sequences of the user administering the medication according to the one or more predetermined actions,
analyzing the captured one or more video sequences to extract determinations of user behavior in a plurality of categories,
calculating, based on the determinations of the user behavior and a user-specific prior determination of cheating probability, a cheating indicator, wherein the user-specific prior determination of cheating probability is based on the initial determination of cheating probability,
updating the user-specific prior determination of cheating probability based on the cheating indicator indicating that the user is not properly administering the medication, wherein updating the user-specific prior determination of cheating probability results in de-weighting the initial determination of cheating probability in the user-specific prior determination of cheating probability, and
adaptively performing a follow-up operation in response to the cheating indicator indicating that the user is not properly administering the medication.

\* \* \* \* \*